United States Patent
Miller

(10) Patent No.: US 9,775,585 B2
(45) Date of Patent: Oct. 3, 2017

(54) VARIABLE POWER SAVING PROCESSING SCHEME FOR ULTRASOUND BEAMFORMER FUNCTIONALITY

(75) Inventor: Gregg Miller, Boulder, CO (US)

(73) Assignee: TOSHIBA MEDICAL SYSTEMS CORPORATION, Otawara-Shi (JP)

( * ) Notice: Subject to any disclaimer, the term of this patent is extended or adjusted under 35 U.S.C. 154(b) by 367 days.

(21) Appl. No.: 13/161,024

(22) Filed: Jun. 15, 2011

(65) Prior Publication Data

US 2012/0323121 A1   Dec. 20, 2012

(51) Int. Cl.
*A61B 8/00*   (2006.01)
*G01S 7/52*   (2006.01)

(52) U.S. Cl.
CPC .............. *A61B 8/56* (2013.01); *A61B 8/4488* (2013.01); *G01S 7/52034* (2013.01); *G01S 7/52096* (2013.01)

(58) Field of Classification Search
CPC ..... A61B 8/4488; A61B 8/56; G01S 7/52034; G01S 7/52096
(Continued)

(56) References Cited

U.S. PATENT DOCUMENTS 6,123,670 A * 9/2000 Mo ................................ 600/447
6,471,651 B1 10/2002 Hwang et al.
(Continued)

FOREIGN PATENT DOCUMENTS

CN       101061452 A    10/2007
JP    2001-0276064 A    10/2001
(Continued)

OTHER PUBLICATIONS

English translation of Shimizu (JP 2006-346161) provided by IPDL.*

(Continued)

*Primary Examiner* — Katherine Fernandez
(74) *Attorney, Agent, or Firm* — Kenichiro Yoshida

(57) ABSTRACT

In general, embodiments of the ultrasound imaging system save power in relation to a predetermined active aperture and or a predetermined update depth. With respect to a predetermined active aperture, the imaging system saves power by reducing or turning off a predetermined portion of the receive electronics when the predetermined receive electronics portion is not operating in relation to the active aperture range. That is, in a first power saving mode, the predetermined receive electronics portion operates only when it is collecting and or processing the data inside the active aperture range. Furthermore, with respect to a predetermined update depth, the imaging system saves power by reducing the operational frequency as the predetermined receive electronics portion collects or process the data from a deeper area. That is, in a second power saving mode, the predetermined receive electronics portion operates less frequently when it is collecting and or processing the data from the middle or far range than the near range. Lastly, the imaging system saves power by modifying the operation as the predetermined receive electronics portion collects or process the data depending upon the active aperture and or the update depth. That is, in a third power saving mode, the predetermined receive electronics portion operates at least less frequently when it is collecting and or processing the data from the outside the active aperture and or at a far update depth. In other words, the third power saving mode is a hybrid or combination of the first and second power saving modes.

2 Claims, 13 Drawing Sheets

(58) Field of Classification Search
USPC .................................. 600/437, 443; 382/128
See application file for complete search history.

(56) References Cited

U.S. PATENT DOCUMENTS

| | | | |
|---|---|---|---|
| 6,527,719 | B1 | 3/2003 | Olsson et al. |
| 8,213,467 | B2* | 7/2012 | Little et al. .................... 370/537 |
| 2004/0252894 | A1* | 12/2004 | Miyanohara ......... H04N 19/176 382/232 |
| 2005/0010111 | A1* | 1/2005 | Kristoffersen ................ 600/437 |
| 2005/0228284 | A1 | 10/2005 | Baumgartner et al. |
| 2006/0058652 | A1 | 3/2006 | Little |
| 2006/0173338 | A1* | 8/2006 | Ma et al. ...................... 600/456 |
| 2007/0239001 | A1* | 10/2007 | Mehi et al. .................... 600/437 |
| 2007/0276236 | A1* | 11/2007 | Jong ........................ A61B 8/00 600/437 |
| 2009/0150692 | A1 | 6/2009 | Poland |
| 2010/0262009 | A1* | 10/2010 | Lynch et al. .................. 600/455 |
| 2010/0268083 | A1* | 10/2010 | McLaughlin et al. ........ 600/443 |

FOREIGN PATENT DOCUMENTS

| | | |
|---|---|---|
| JP | 2006-346161 A | 12/2006 |
| JP | 2008-520314 A | 6/2008 |
| JP | 2012-055559 A | 3/2012 |

OTHER PUBLICATIONS

International Search Report for corresponding International Application No. PCT/JP2012/065356 mailed on Sep. 11, 2012.
Chinese Office Action with its English Summary for Chinese Patent Application No. 201280001248.9 mailed on Mar. 2, 2015.

* cited by examiner

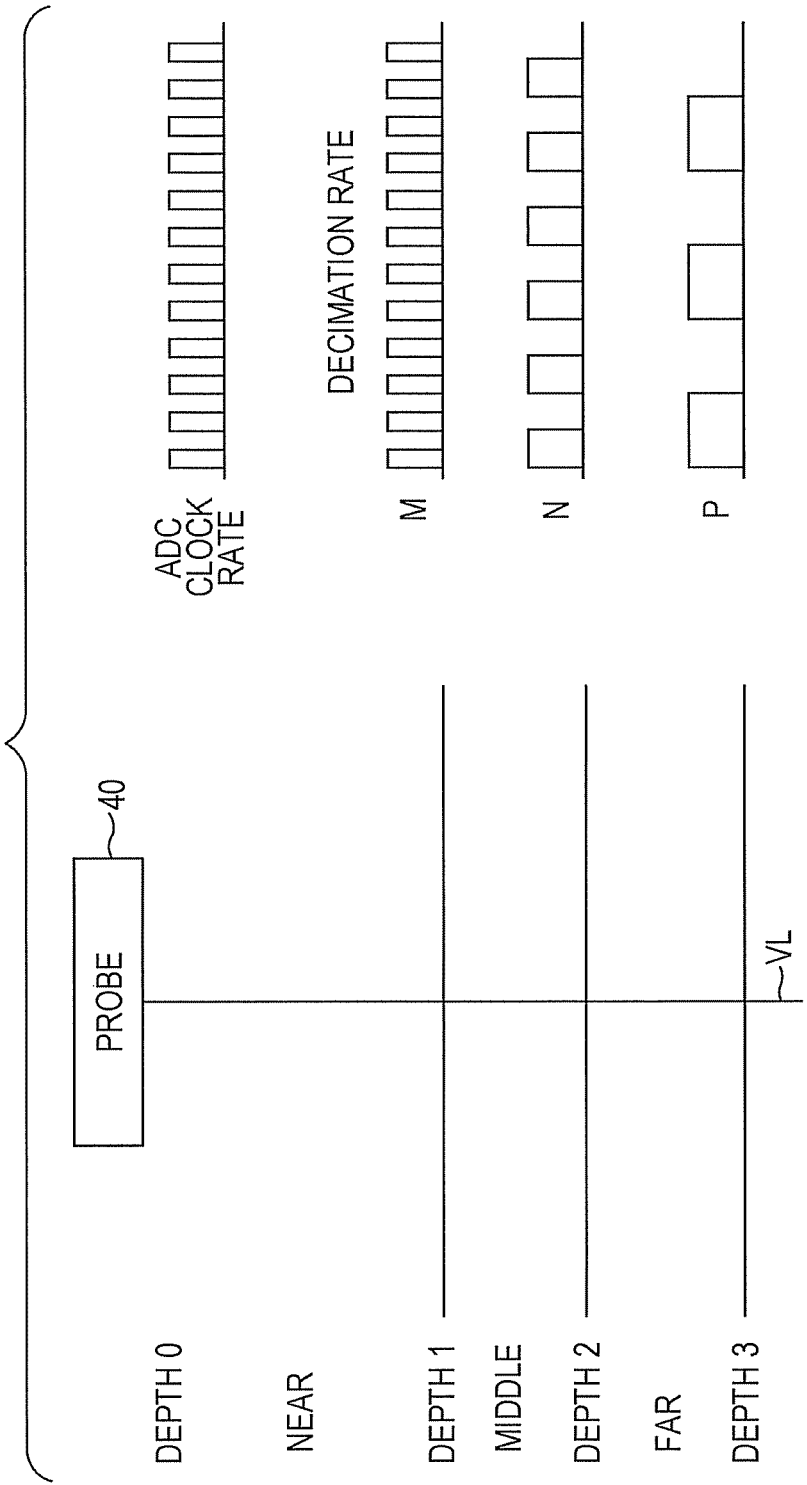

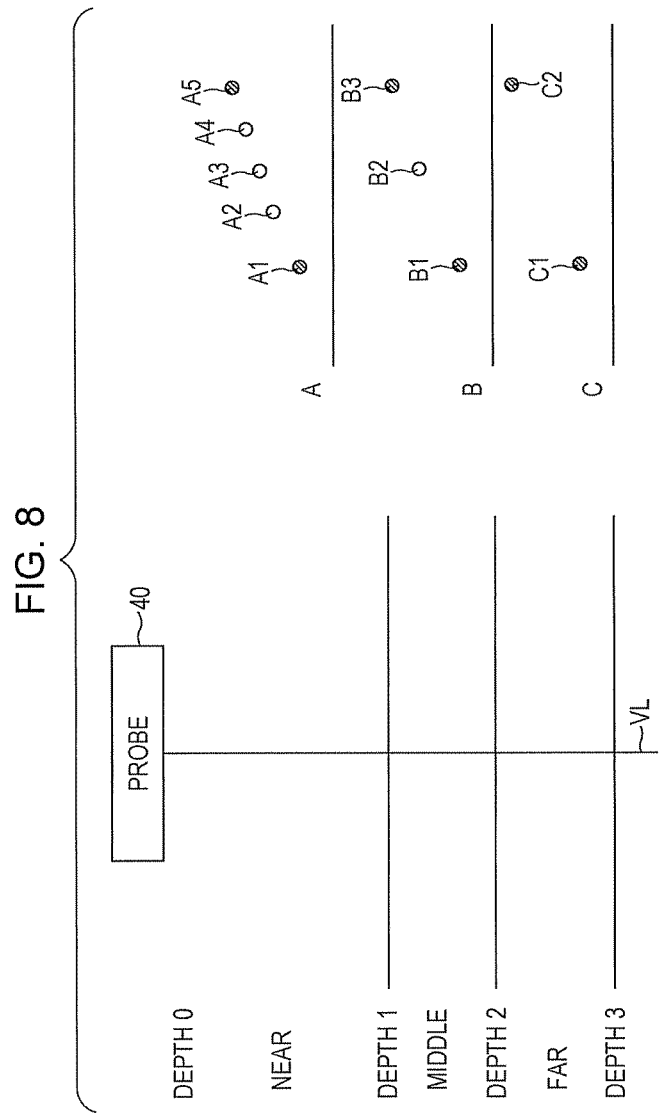

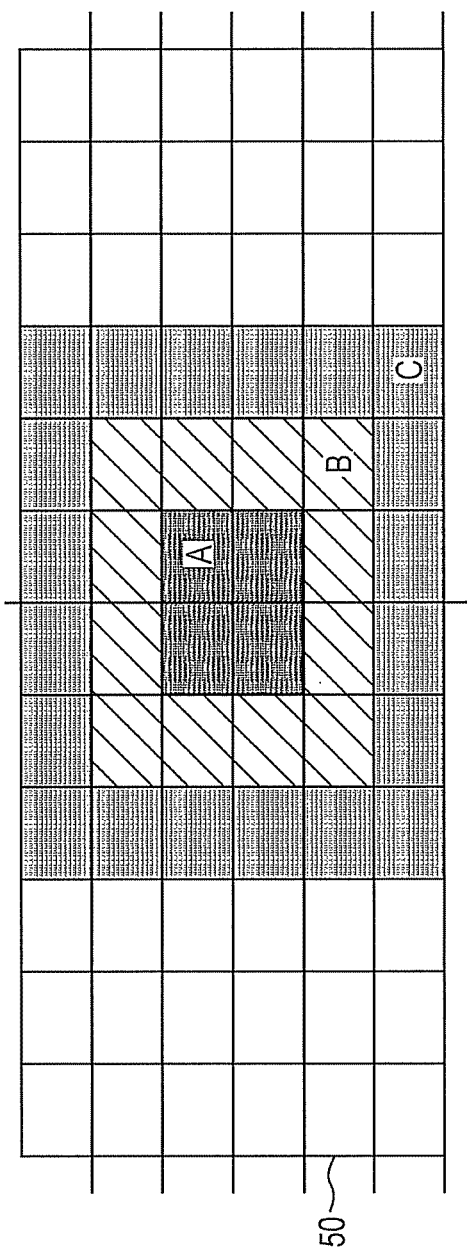
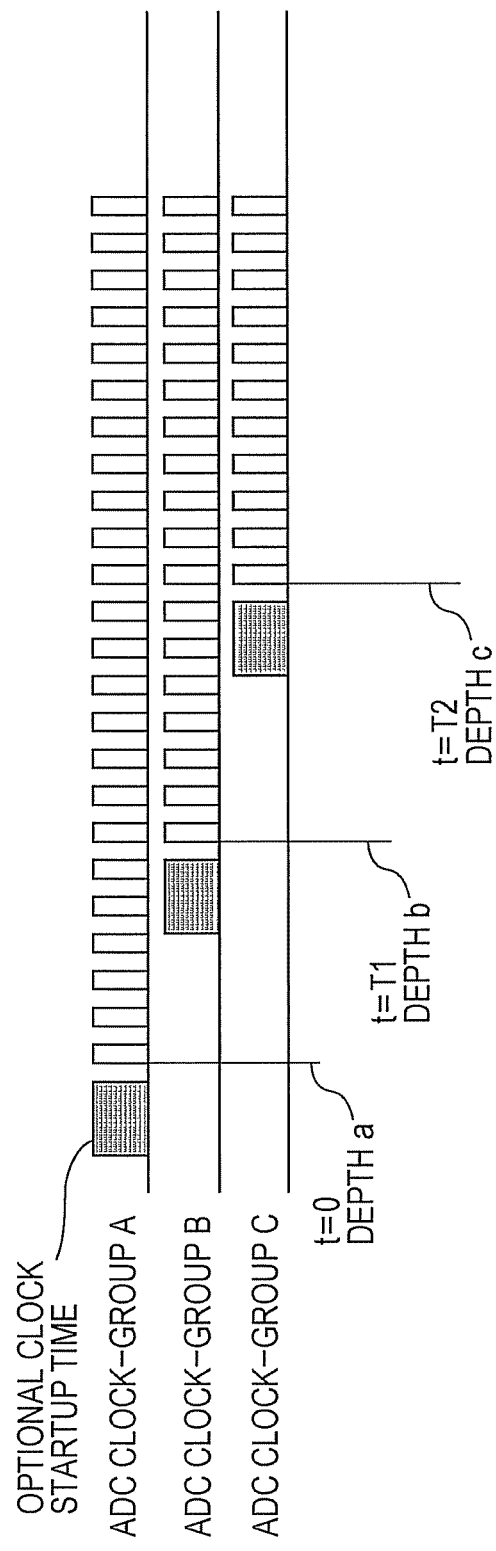
FIG. 9A
FIG. 9B

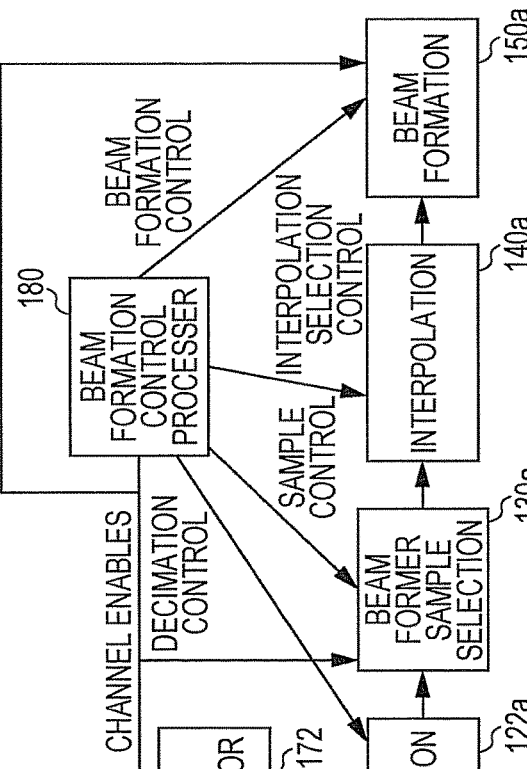
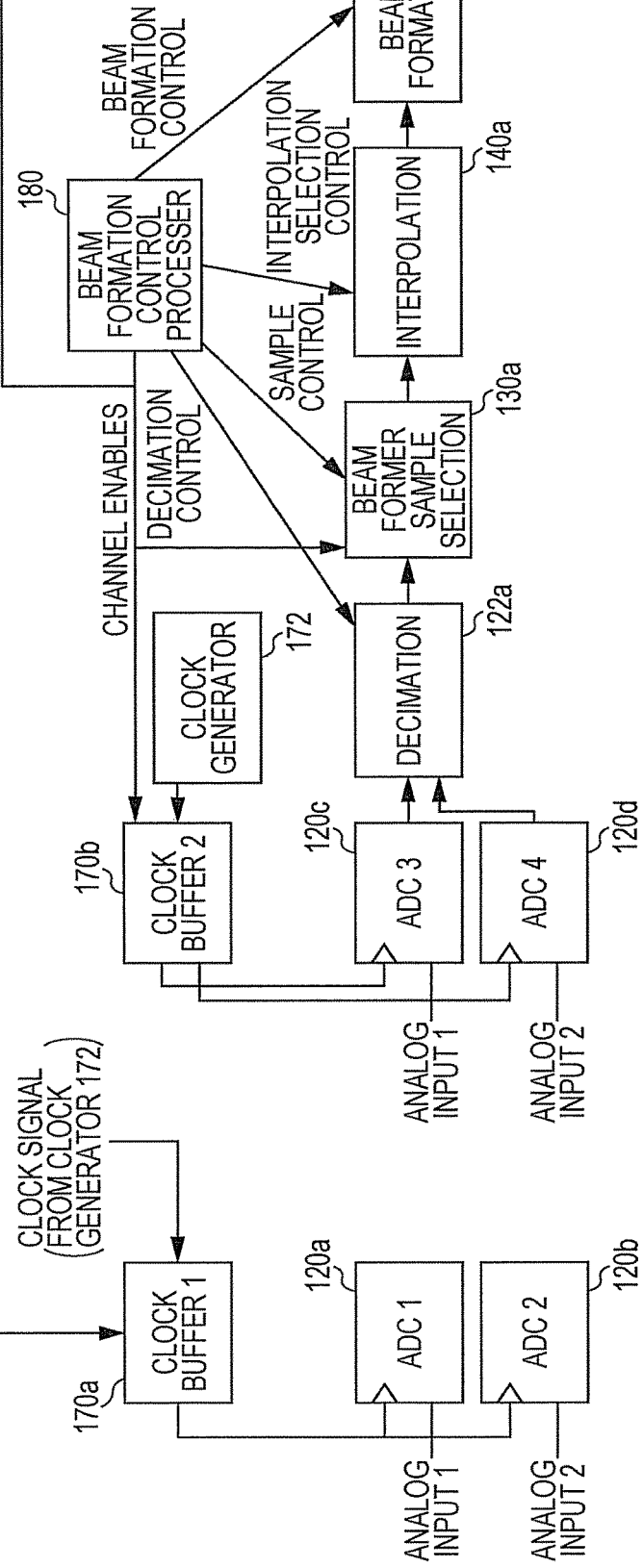
FIG. 12A
FIG. 12B

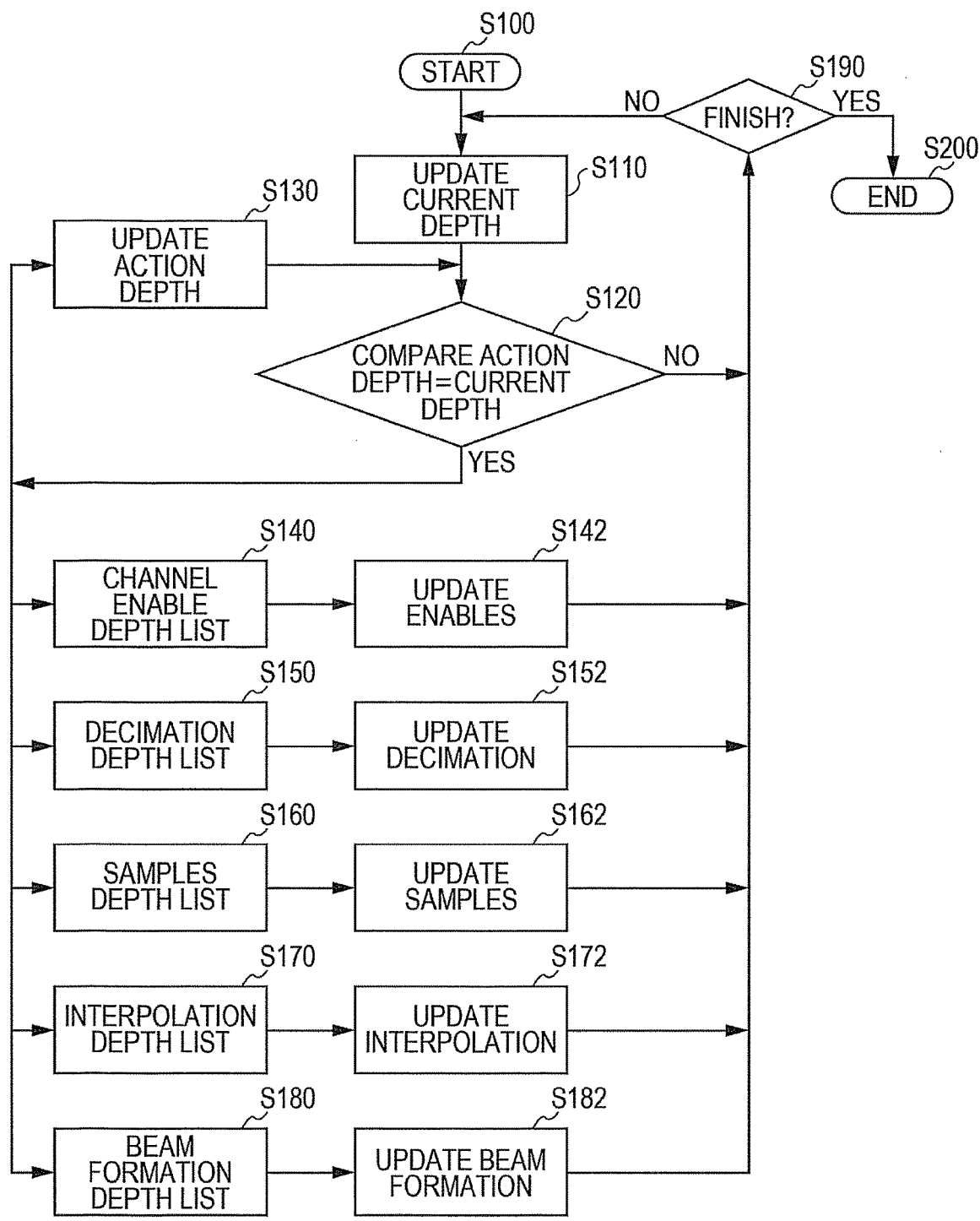

VARIABLE POWER SAVING PROCESSING SCHEME FOR ULTRASOUND BEAMFORMER FUNCTIONALITY

FIELD

Embodiments described herein generally relate to power saving for ultrasound diagnostic imaging systems and methods of operating the same.

BACKGROUND

To save power in ultrasound diagnostic imaging systems and method of operating the same, prior attempts have been made to turn off certain circuits or reduce power consumption in these or other circuits during the operation. These attempts are either by turning off or reducing power consumption of the circuits that are unnecessary or idle during certain phases of the operation. As the powered-down circuits are needed again during certain other phases of the operation, the ultrasound imaging system increases power consumption in these circuits to an operable level. Obviously, although these attempts save some power consumption, they also require additional controls.

The additional controls may involve some trade-offs. For example, since power-down and power-up require an additional amount of time, the efficiency in the ultrasound imaging system may be compromised. In another trade-off, the image quality may be compromised due to the lack of the stable power in certain image processing circuits.

One way to improve power consumption in the ultrasound diagnostic imaging systems is related to controlling various processing units based upon the delayed time characteristics of the reflected ultrasound signals that are received at the probe.

BRIEF DESCRIPTION OF THE DRAWINGS

FIG. 7 is a diagram illustrating a varying decimation rate of the decimator unit at different update depths in the second embodiment of the ultrasound imaging system according to the current invention.

FIG. 8 is a diagram illustrating a varying Sample Interpolation Rate of the sample interpolation unit at different update depths in the second embodiment of the ultrasound imaging system according to the current invention FIG. 9 includes diagrams illustrating another power saving scheme based upon a combination of the active aperture and the update depth in a third embodiment of the ultrasound imaging system according to the current invention.

FIG. 12 is a diagram illustrating in a sixth embodiment for processing the ultrasound data while saving power in an imaging system according to the current invention.

FIG. 13 is a flow chart illustrating an exemplary process that generally relies upon a set of predetermined depths and initiates a combination of predetermined operations for saving power at each of the predetermined depths.

DETAILED DESCRIPTION

Embodiments of the ultrasound imaging system according to the current invention include a probe or transducer unit, a processing unit and a cable connecting the probe to the processing unit. In general, the embodiments of the probe include some structures, components and elements of a conventional ultrasound probe. That is, one embodiment of the probe generates ultrasound pulses and transmits them towards a certain area of a patient. The embodiment also receives the ultrasound echoes reflected from the patient. While many embodiments of the probe are generally connected to the processing unit via a cable and hand-held devices, the probes are not limited to these structural requirements in order to practice the current invention.

Figure 1:
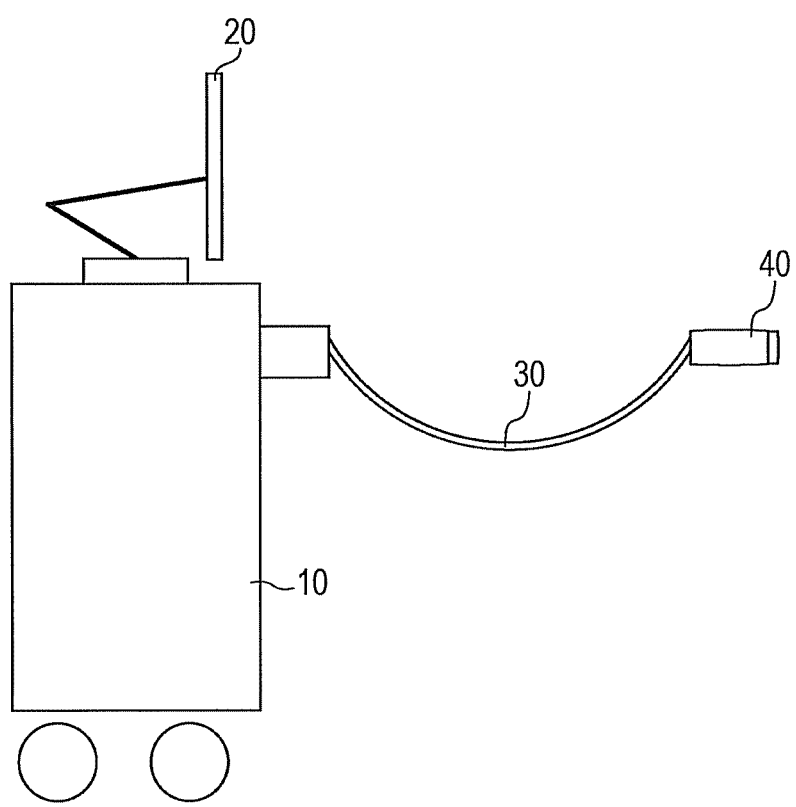
FIG. 1 is a diagram illustrating one embodiment of the ultrasound imaging system according to the current invention.

As illustrated in FIG. 1, one embodiment of the ultrasound imaging system according to the current invention includes a system unit 10, a cable 30 and an ultrasound probe handle 40. The probe 40 is connected to the system 10 via the cable 30. The system unit 10 generally controls a transducer such as a 2-dimensional array in the probe handle 40 for transmitting ultrasound pulses towards a region of interest in a patient and receiving the ultrasound echoes reflected from the patient. The system unit 10 concurrently receives in real time the reflected ultrasound signals or echoes for further processing so as to display on a display unit 20 an image of the region of the interest. In the above described embodiment of the ultrasound imaging system, the probe unit 40 sends the system unit 10 via the cable 30 a large volume of reflected ultrasound data for real-time imaging. In other embodiments, the data are wirelessly sent between the transducer unit 40 and the system unit 10.

Figure 2:
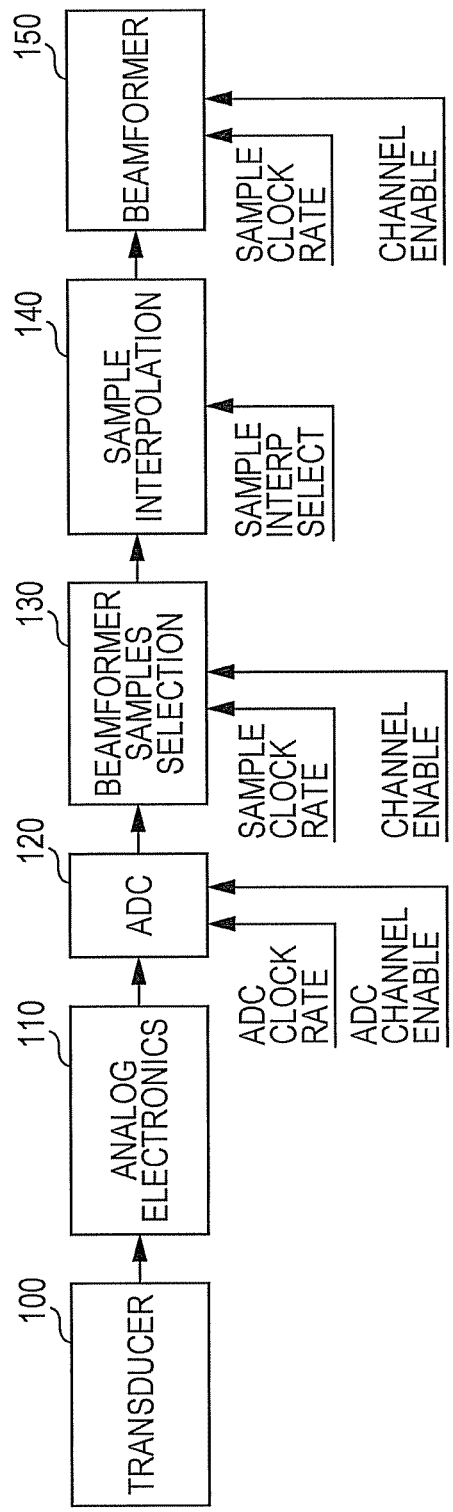
FIG. 2 is a diagram illustrating functional blocks for collecting ultrasound data and processing the data to generate images in one embodiment according to the current invention.

Now referring to FIG. 2, a diagram illustrates functional blocks for collecting ultrasound data and processing the data to generate images in one embodiment according to the current invention. In one embodiment, the functional blocks include a transducer block 100, an analog electronics block 110, an analogue-to-digital converter (ADC) block 120, a beamformer sample selection block 130, a sample interpolation block 140 and a beamformer block 150. The above functional blocks are optionally implemented by corresponding hardware units and software module in one embodiment. The above functional blocks are also optionally implemented by a combination of hardware units and software modules that do not necessarily correspond to the functional blocks 100 through 150 in another embodiment. Furthermore, all or some of these functional blocks are optionally implemented on the probe 40 according to the current invention.

For the purpose of the current patent application, a power saving unit optionally includes a combination of the analog electronics block 110, the analogue-to-digital converter (ADC) block 120, the beamformer sample selection block 130, the sample interpolation block 140 and the beamformer block 150.

The transducer 100 is generally located in the probe 40. The transducer 100 further includes transmit and receive elements such as a 2-dimensional transducer array having a predetermined number of transducer elements, which are grouped into channels for transmitting the ultrasound pulses and receiving the ultrasound echoes or both. For 2-dimensional (2D) imaging data, a number of channels ranges from 64 to 256. On the other hand, for 3-dimensional (3D) imaging data, a number of required channels often exceeds 1000's.

The transducer 100 additionally may include transmit electronics and receive electronics such that the transducer 100 transmits ultrasound pulses from transmit elements towards a region of interest of a subject and properly receives ultrasound echoes that have been reflected from the region of interest of the subject at a first predetermined number of receiving elements of the transducer array so that the ultrasound echoes are converted into a first predetermined number of channel signals. Although the current invention is not limited, the number of the transmit elements and the receive elements are generally the same. Furthermore, the current invention is also not limited to the use of a two-dimensional transducer array.

Embodiments of the probe 40 also include the analog electronics 110 for processing 2D and or 3D/4D data that is received at the transducer 100. For example, the receive analogue electronics 110 performs a predetermined sequence of signal processing on the input from the transducer 100. The transducer 100 utilizes a predetermined number of N receive elements, which output N number of channel signals. In certain situation, the transducer 100 optionally utilizes less than all of the available receive elements. Thus, the analogue electronics 110 receives the N-channel signals from the transducer 100 via connections. In one exemplary embodiment, the analogue electronics 110 includes a processing unit which is a combination of devices such as a low noise amplifier (LNA) and a voltage gain amplifier. In one particular exemplary embodiment, the LNA initially performs low noise amplification on the N-channel signals directly received from the transducer 100. The LNA amplifies signals while it matches input impedance to element impedance for maximum signal-to-noise ratio and bandwidth. Subsequently, a Depth Gain Compensation (DGC) amplifier performs gain amplification on the output from the LNA in this particular exemplary embodiment. The DGC amplifies signals, and the gain changes with time and or depth.

After every one of the signals from the transducer 100 has been pre-processed by the analogue electronics 100, an analog-to-digital signal converter (ADC) 120 selectively performs an analog-to-digital signal conversion on the signal from the preprocessed signal. A resolution level of the analog-to-digital conversion is related to a ratio between a reduced number of output channels and an original number of input channels in the connecting or switching operation.

In addition, as will be further discussed for the power saving purposes, the ADC unit 120 selectively performs the ADC conversion based upon a predetermined set of conditions that are specified by a pair of an ADC Clock Rate signal and an ADC Channel Enable signal. That is, unless the ADC unit 120 is selectively enabled by the ADC Channel Enable signal when certain channel is inside a predetermined active aperture, the ADC unit 120 fails to convert the preprocessed data from the Transducer 100. The concept of a predetermined aperture will be described with respect to FIG. 3.

By the same token, as the beamformer sample selection block 130 receives the converted digital signal from the ADC 120, the beamformer sample selection block 130 also selectively accepts the converted data based upon a predetermined set of conditions that are specified by a pair of a Sample Clock Rate signal and a Channel Enable signal. That is, as will be further discussed for the power saving purposes, unless the beamformer sample selection block 130 is enabled by the Channel Enable signal when certain channel is inside a predetermined active aperture, the beamformer sample selection block 130 receives no converted channel sample data from the ADC 120. The concept of a predetermined aperture will be described with respect to FIG. 3. In other words, the beamformer sample selection block 130 functions as a power-saving gate for the down stream blocks which include the sample interpolation block 140 and the beamformer block 150.

Further down the stream from the beamformer sample selection block 130, the sample interpolation block 140 selectively interpolates the selected beamformer sample data based upon a Sample Interpolate Select signal. That is, the sample interpolation block 140 interpolates the selected beamformer sample data from the beamformer sample selection block 130 in a manner to economize the interpolation process for the power saving purposes.

Lastly, the beamformer block 150 selectively generates images from the interpolated beamformer sample data from the sample interpolation block 140 based upon a predetermined set of conditions that are specified by a pair of a Sample Clock Rate signal and a Channel Enable signal. That is, as will be further discussed for the power saving purposes, unless the beamformer 150 is enabled by the Channel Enable signal, the beamformer 150 generates no image from the interpolated sample data from the sample interpolation block 140. In other words, the beamformer 150 economizes the image generation for the power saving purposes.

The above described embodiment according to the current invention saves power in collecting ultrasound data and processing the data to generate images. In general, the embodiment saves power in overall receiver operations for probe electronics. The receive electronics as illustrated in the embodiment operates in a predetermined 1-D or 2-D imaging mode. The detailed power savings will be further described in the following with respect to a particular aspect of the power savings. Furthermore, the embodiment will apply the saved power to any combination of 1) increasing power in various stages, 2) reducing overall power requirements, 3) increasing dynamic range and 4) increasing signal-to-noise ratio. The application of the saved power is not limited to the above illustrated applications.

In general, power is saved in relation to a predetermined active aperture and or a predetermined focusing depth. With respect to a predetermined active aperture, the imaging system saves power by reducing or turning off a predetermined portion of the receive electronics when the predetermined receive electronics portion is not operating in relation to the active aperture range. That is, in a first power saving mode, the predetermined receive electronics portion operates only when it is collecting and or processing the data inside the active aperture range. Furthermore, with respect to a predetermined focus depth, the imaging system saves power by reducing the operational frequency as the predetermined receive electronics portion collects or process the data from a deeper area. That is, in a second power saving mode, the predetermined receive electronics portion operates less frequently when it is collecting and or processing the data from a longer focal point. Lastly, the imaging system saves power by modifying the operation as the predetermined receive electronics portion collects or process the data depending upon the active aperture and or the focus depth. That is, in a third power saving mode, the predetermined receive electronics portion operates at least less frequently when it is collecting and or processing the data from the outside the active aperture and or a longer focal point. In other words, the third power saving mode is a hybrid or combination of the first and second power saving modes.

Figure 3:
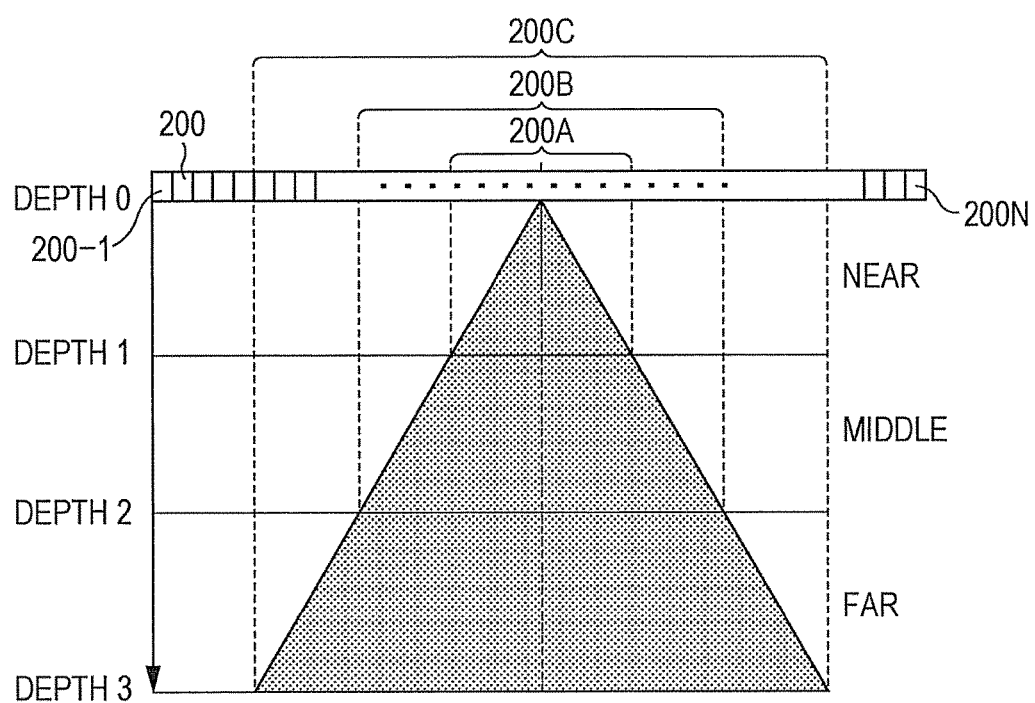
FIG. 3 is a diagram illustrating one exemplary relation between a focusing depth and an active aperture size in the ultrasound imaging system according to the current invention.

Now referring to FIG. 3, a diagram illustrates one exemplary relation between a focusing depth and an active aperture size in the ultrasound imaging system according to the current invention. For the purpose of this patent disclosure, the term, "aperture" refers to the full size of the transducer element array. On the other hand, the term, "active aperture" refers to the transducer elements that are being utilized at a particular depth in an ultrasound imaging system. Furthermore, for the purpose of this patent disclosure, the terms, "near field," "middle field" and "far field" respectively refer to a relative depth range from the probe receive surface during ultrasound imaging. The near field is the shallowest depth range in a subject with respect to the probe from which the ultrasound is transmitted and received. In this example, the near field is a depth range between a depth 0 and a predetermined depth 1. The depth 0 is near or at the transducer surface. The far field is the deepest depth range in the subject with respect to the probe from which the ultrasound is transmitted and received. In this example, the far field is a depth range between a depth 2 and a predetermined depth 3. The middle field is a depth range between the near field and the far field in the subject. In this example, the middle field is a depth range between the depth 1 and the predetermined depth 2. These fields are generally not overlapping.

Still referring to FIG. 3, the active aperture grows as a focus point deepens in one embodiment of the ultrasound imaging system according to the current invention. A transducer 200 includes a predetermined number of elements 200-1 through 200-N. In the near field, an active aperture corresponds to a predetermined set of transducer elements 200A. In the middle field, an active aperture corresponds to a predetermined set of transducer elements 200B which includes the transducer elements 200A but is larger than the transducer elements 200A. In the far field, an active aperture corresponds to a predetermined set of transducer elements 200C which includes the transducer elements 200B but is larger than the transducer elements 200B. The near filed active aperture elements 200A basically project outward so that the focusing is directly related to the size of the active aperture. On the other hand, at deeper depths, the electronic focusing becomes dominant. For this reason, on receive, a small active aperture is used near the probe face. A larger active aperture is used as the depth increases until the full probe aperture is being used. To practice the current invention, although the aperture growth is helpful in saving power, it is not necessary to grow the active aperture size as the focus deepens.

The active receive aperture size is calculated at each depth. In general, a receive aperture size is determined based upon a desired f number, which is related to a distance from the surface of the probe face. In further detail, the f number value is determined by an active aperture size divided by a corresponding depth. A typical value off number is 1 or 2. Assuming that a certain maximum aperture is required for a sufficient level of imaging performance, as the aperture size is reduced in the near field while the aperture size is enlarged to the required maximum size, the power is saved in one embodiment of the ultrasound medical imaging system due to the less power consumption by the smaller active aperture size in the receive transducer for the near and or middle field. Furthermore, an additional amount of power saving is realized by the reduced data in the subsequent processing steps at the devices or units located in a down stream of an embodiment of the ultrasound imaging system according to the current invention.

Figure 4:
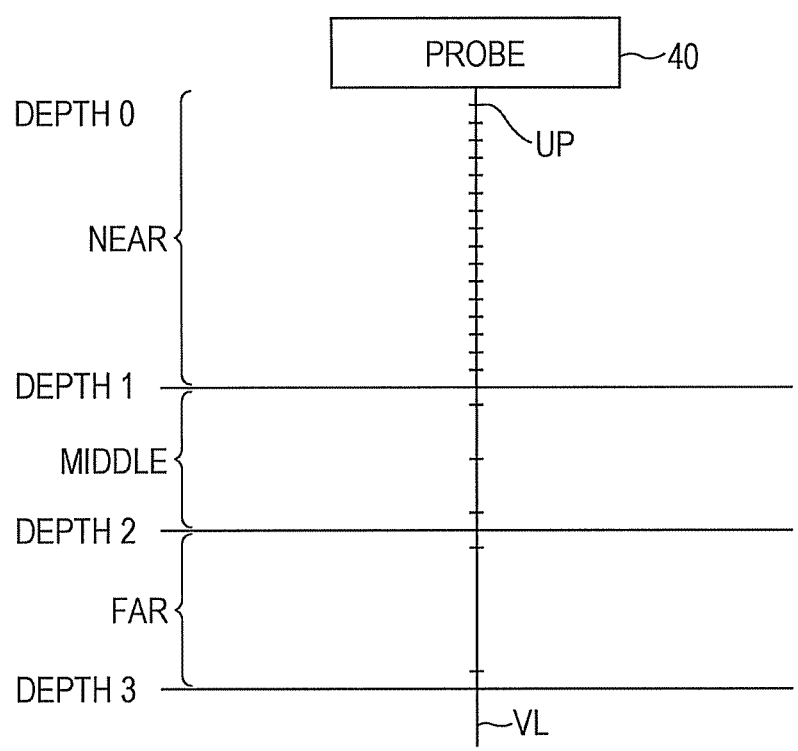
FIG. 4 is a diagram illustrating update frequency rates at different focusing depths in one embodiment of the ultrasound imaging system according to the current invention.

Now referring to FIG. 4, a diagram illustrates update frequency rates at different focusing depths in one embodiment of the ultrasound imaging system according to the current invention. As already described above with respect to FIG. 3, the near field is the shallowest depth range in a subject with respect to the probe 40 from which the ultrasound is transmitted and received, and its depth ranges between a depth 0 and a predetermined depth 1. The middle field is a depth range between the near field and the far field in the subject, and its depth ranges between the predetermined depth 1 and a predetermined depth 2. The far field is the deepest depth range in the subject with respect to the probe, and its depth ranges between the depth 2 and a predetermined depth 3. These fields are generally not overlapping.

Still referring to FIG. 4, a vertical line VL from the probe 40 indicates one direction of an arbitrary ultrasound pulse along the update depth (UD) while horizontal lines UD perpendicular to the vertical line VL signify updates or update functions. In each of the three depth ranges, a single horizontal line UD indicates a predetermined number of update events at a predetermined particular depth, and a total number of the updates within a given depth range determines an update frequency rate for the depth range. During each update function, one embodiment of the ultrasound imaging system according to the current invention performs a predetermined set of processing functions on a selected data set. In one embodiment of the ultrasound imaging system according to the current invention as described with respect to FIG. 2, a single update event involves processing of the selected ultrasound data at the analog-to-digital signal converter (ADC) 120, the beamformer sample selection block 130, the sample interpolation block 140 and the beamformer block 150. Furthermore, a single update event also optionally involves a step of updating the aperture size. In one embodiment, the update events sequentially decrease the update frequency as the update depth increases. In another embodiment, the update events decrease the update frequency while increase the aperture size as the update depth increases. The definition of the single update is not limited to the above described units and optionally includes a different combination of the units or devices in other embodiments.

As illustrated in FIG. 4, the update frequency rate varies among the depth ranges. For example, one embodiment of the ultrasound imaging system according to the current invention performs sixteen updates UDs as indicated by the horizontal bars in the near field between the depth 0 and the depth 1. In the same example, the embodiment of the ultrasound imaging system performs three updates UDs as indicated by the horizontal bars in the middle field between the depth 1 and the depth 2. Lastly, the embodiment of the ultrasound imaging system performs two updates UDs as indicated by the horizontal bars in the far field between the depth 2 and the depth 3. As illustrated in the above example, the update frequency decreases as the depth increases along the ultrasound pulse. In other words, in the near field between the depth 0 and the depth, the embodiment of the ultrasound imaging system according to the current invention performs the updates at a higher rate than the in the middle or far ranges. Consequently, the updates also take place within a shorter distance between the focusing points in the near field than the middle or far field as indicated by the update positions UDs. As the distance from the probe 40 increases in the middle or far field, the aperture size optionally grows without compromising sidelobe or focusing characteristics in one embodiment according to the current invention.

As an update takes place at a different depth, each channel is updated in one exemplary process. In other words, all of the channels are updated at each of the predetermined update depths. In another exemplary process, different channels are updated at each of the slightly different depth, and this is optionally accomplished by separating by a clock. The clock-based implementation allows the same hardware to be utilized for multiple channels by clocking at a higher rate in order to save hardware resources. In summary, all channels are optionally updated at the same depth or slightly differing depths.

In combination with the above described varying update frequency, the aperture size optionally changes in one embodiment of the ultrasound imaging system according to the current invention. Thus, the combined features in one embodiment provide the higher update rate and the smaller active aperture size in the near field while the lower update rate and the larger active aperture size in the middle or far field. These combined features are not necessary to practice in the current invention, and these features are optionally performed in an independent manner in other embodiments according to the current invention.

Figure 5:
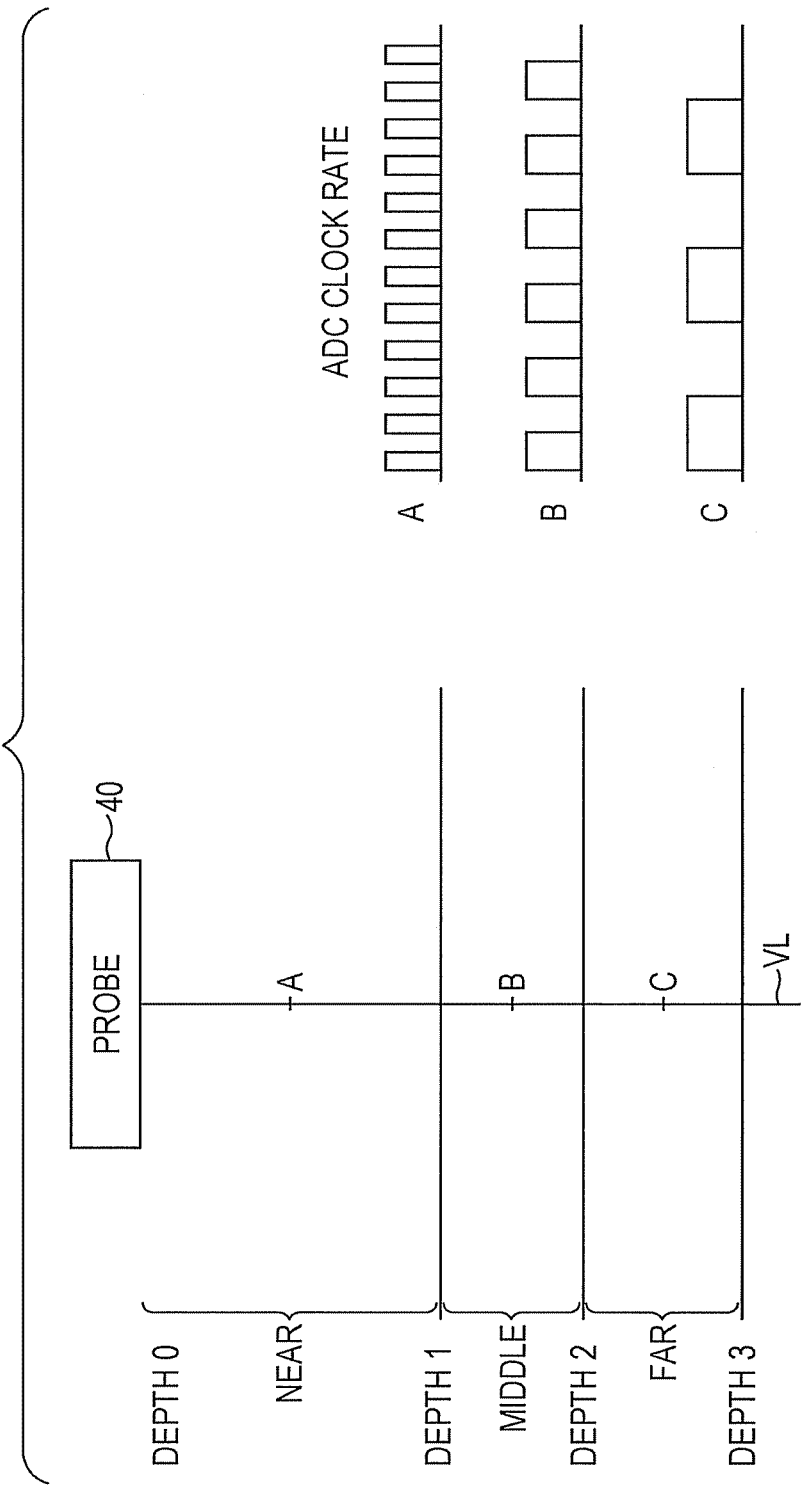
FIG. 5 is a diagram illustrating a sampling frequency of the analog-to-digital conversion (ADC) at different focusing depths in one embodiment of the ultrasound imaging system according to the current invention.

Now referring to FIG. 5, a diagram illustrates a sampling frequency of the analog-to-digital conversion (ADC) at different focusing depths in one embodiment of the ultrasound imaging system according to the current invention. As already described above with respect to FIG. 3, the near field is the shallowest depth range in a subject with respect to the probe 40 from which the ultrasound is transmitted and received, and its depth ranges between a depth 0 and a predetermined depth 1. The middle field is a depth range between the near field and the far field in the subject, and its depth ranges between the predetermined depth 1 and a predetermined depth 2. The far field is the deepest depth range in the subject with respect to the probe, and its depth ranges between the depth 2 and a predetermined depth 3. These fields are generally not overlapping.

Still referring to FIG. 5, three particular depth ranges A, B and C are respectively located in the near, middle and far range as indicated along a vertical line VL. At each of these predetermined depths, the ADC takes place at a predetermined sample rate as illustrated by the corresponding ADC clock rate. In the current application, the sample rate, the sampling frequency, the clock rate and the clock frequency are used in a roughly synonymous manner although these terms do not necessarily and strictly refer to the same rate or frequency in certain other implementations in the relevant art. That is, an analog-to-digital converter receives the channel signals and samples at a predetermined sampling frequency in one embodiment according to the current invention. Since the analog-to-digital converter requires higher power levels at higher sampling frequencies, power is saved as the sample rate decreases. For this reason, one embodiment of the analog-to-digital converter in the ultrasound imaging system operates based upon a varying ADC clock rate at the corresponding update depth according to the current invention.

As illustrated in FIG. 5, an analog-to-digital converter samples at the highest ADC clock frequency at an exemplary update depth A in the near field for best sidelobe performance while the same analog-to-digital converter samples at the lowest ADC clock frequency at an exemplary update depth C in the far field for the lack of substantial sidelobe issues. At an exemplary update depth B in the middle field, the analog-to-digital converter samples at a third ADC clock frequency that is between the highest and lowest ADC clock frequencies for the sufficiently low sidelobe effects. As a result of the higher sampling frequency, the analog-to-digital converter samples more samples per second. For example, in one embodiment of the probe operating at 5 MHz, the ADC rate is approximately 90 mega samples per second (MSPS) in the near field, 67.5 MSPS in the middle field and 45 MSPS in the far field. The above exemplary depths or ranges are not limited to any particular number such as three.

Figure 6:
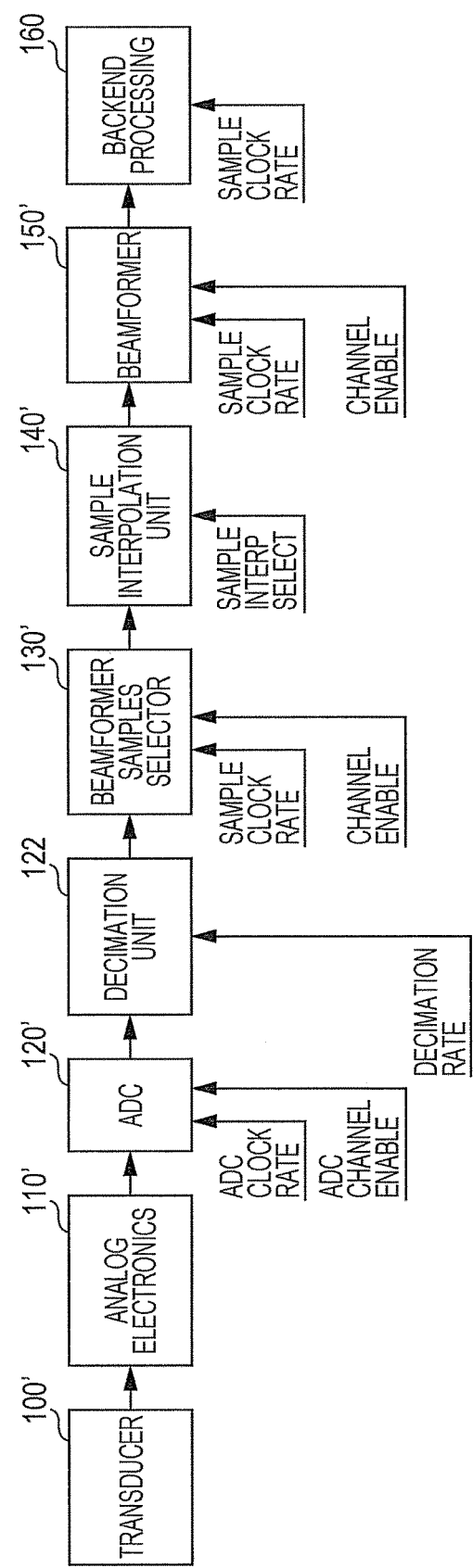
FIG. 6 is a diagram illustrating functional blocks for collecting ultrasound data and processing the data to generate images in a second embodiment according to the current invention.

Now referring to FIG. 6, a diagram illustrates functional blocks for collecting ultrasound data and processing the data to generate images in a second embodiment according to the current invention. In the second embodiment, the functional blocks include a transducer block 100', an analog electronics block 110', an analogue-to-digital converter (ADC) block 120', a decimator block 122, a beamformer sample selection block 130', a sample interpolation block 140', a beamformer block 150' and a backend processing block 160. The above functional blocks are optionally implemented by corresponding hardware units and software modules in one embodiment. The above functional blocks are also optionally implemented by a combination of hardware units and software modules that do not necessarily correspond to the functional blocks 100 through 160 in another embodiment. Furthermore, all or some of these functional blocks are optionally implemented on the probe 40 according to the current invention.

For the purpose of the current patent application, a power saving unit optionally includes a combination of the analog electronics block 110', the analogue-to-digital converter (ADC) block 120', the decimator block 122, the beamformer sample selection block 130', the sample interpolation block 140' and the beamformer block 150'.

The transducer 100' is generally located in the probe 40. The transducer 100' further includes transmit and receive elements such as a 2-dimensional transducer array having a predetermined number of transducer elements, which are grouped into channels for transmitting the ultrasound pulses and receiving the ultrasound echoes. For 2-dimensional (2D) imaging data, a number of channels ranges from 64 to 256. On the other hand, for 3-dimensional (3D) imaging data, a number of required channels often exceeds 1000's.

The transducer 100' additionally includes optional transmit electronics and receive electronics such that the transducer 100' transmits ultrasound pulses from transmit elements towards a region of interest of a subject and properly receives ultrasound echoes that have been reflected from the region of interest of the subject at a first predetermined number of receiving elements of the transducer array so that the ultrasound echoes are converted into the first predetermined number of channel signals or fewer. Although the current invention is not limited, the number of the transmit elements and the receive elements are generally the same. Furthermore, the current invention is also not limited to the use of a two-dimensional transducer array.

Embodiments of the probe 40 also include the analog electronics 110' for processing 2D and or 3D/4D data that is received at the transducer 100'. For example, the receive analogue electronics 110' performs a predetermined sequence of signal processing on the input from the transducer 100'. The transducer 100' utilizes a predetermined number of N receive elements, which output N number of channel signals or fewer. In certain situation, the transducer 100' optionally utilizes less than all of the available receive elements. Thus, the analogue electronics 110' receives the N-channel signals or fewer from the transducer 100' via connections. In one exemplary embodiment, the analogue electronics 110' includes a processing unit, which is a combination of devices such as a low noise amplifier (LNA) and a voltage gain amplifier. In one particular exemplary embodiment, the LNA initially performs low noise amplification on the N-channel signals or fewer directly received from the transducer 100'. The LNA amplifies signals while it ideally matches input impedance to element impedance for maximum signal-to-noise ratio and bandwidth. Subsequently, a Depth Gain Compensation (DGC) amplifier performs gain amplification on the output from the LNA in this particular exemplary embodiment. The DGC amplifies signals while gain changes with time and or depth.

After the analogue electronics 100' has processed every one of the signals from the transducer 100', an analog-to-digital signal converter (ADC) 120' selectively performs an analog-to-digital signal conversion on the signal from the processed signal. A resolution level of the analog-to-digital conversion is related to a ratio between a reduced number of output channels and an original number of input channels in the connecting or switching operation. In addition, as will be further discussed for the power saving purposes, the ADC unit 120' selectively performs the ADC conversion based upon a predetermined set of conditions that are specified by an ADC Clock Rate signal and a corresponding ADC Channel Enable signal. For example, unless the ADC unit 120' is selectively enabled by the ADC Channel Enable signal when certain channel is inside a predetermined active aperture, the ADC unit 120' fails to convert the preprocessed data from the Transducer 100'. In one implementation of the second embodiment, the ADC Clock Rate signal determines an ADC sampling rate at the ADC 120', and alternatively the ADC Clock Rate signal has a constant rate across the update depths.

In the second embodiment of the ultrasound imaging system according to the current invention, a decimator unit 122 is connected to the ADC 120' for receiving the digital outputs from the ADC 120'. The decimator unit 122 further processes the number of converted sample outputs from the ADC 120' depending upon a decimation rate signal which may reflect the update depth. That is, the decimator unit 122 reduces a number of the converted sample outputs from the ADC 120' as the update depth increases in order to have substantially the same effect on image performance as changing sampling rates. The decimator function will be further described with respect to FIG. 7.

By the same token, as the beamformer sample selection block 130' receives the selected converted digital data from the decimator unit 122, the beamformer sample selection block 130' also selectively accepts the converted data based upon a predetermined set of conditions that are specified by a pair of a Sample Clock Rate signal and a Channel Enable signal. For example, as will be further discussed for the power saving purposes, unless the beamformer sample selection block 130' is enabled by the Channel Enable signal when a certain channel is inside a predetermined active aperture, the beamformer sample selection block 130' receives no converted channel sample data from the ADC 120'. The concept of a variable aperture will be described with respect to FIG. 10. In other words, the beamformer sample selection block 130' functions as a power-saving gate for the down stream blocks which include the sample interpolation block 140' and the beamformer block 150'.

Further down the stream from the beamformer sample selection block 130', the sample interpolation block 140' selectively interpolates the selected beamformer sample data based upon a Sample Interpolate Select signal. That is, the sample interpolation block 140' interpolates the selected beamformer sample data from the beamformer sample selection block 130' in a manner to optimize image fidelity properties while economizing the interpolation process for power saving purposes where image infidelity issues are minimally impacted by reducing sample interpolation.

In addition, the beamformer block 150' sums the interpolated channel sample data from the sample interpolation blocks 140' based upon a predetermined set of conditions that are specified by a pair of a Sample Clock Rate signal and a Channel Enable signal. That is, as will be further discussed for the power saving purposes, unless a beamformer channel in 150' is enabled by the Channel Enable signal, the particular beamformer channel in 150' generates no samples from the interpolated sample data from the sample interpolation block 140'. In other words, the beamformer 150' economizes the rf data summation generation for power saving purposes.

Lastly, the second embodiment of the ultrasound imaging system according to the current invention includes a backend processing block 160. Upon receiving the beamformed signal data from the beamformer block 150', the backend processing block 160 further processes the beamformer rf data before the image is scan converted and displayed.

The above described embodiment according to the current invention saves power in collecting ultrasound data and processing the data to generate images. In general, the embodiment saves power in overall receiver operations for probe electronics. The receive electronics as illustrated in the embodiment operates in a predetermined 1-D or 2-D imaging mode. The detailed power savings will be further described in the following with respect to a particular aspect of the power savings. Furthermore, the embodiment will apply the saved power to any combination of 1) increasing power in various stages, 2) reducing overall power requirements, 3) increasing dynamic range and 4) increasing signal-to-noise ratio. The application of the saved power is not limited to the above illustrated applications.

In general, power is saved in relation to a predetermined active receive aperture and or a predetermined update depth. With respect to a predetermined active aperture, the imaging system saves power by reducing or turning off a predetermined portion of the receive electronics when the predetermined receive electronics portion is not operating in relation to the active aperture range. That is, in a first power saving mode, the predetermined receive electronics portion operates only when it is collecting and or processing the data inside the active aperture range. Furthermore, with respect to a predetermined update depth, the imaging system saves power by reducing the operational sampling frequency as the predetermined receive electronics portion collects or process the data from a deeper area. In a second power saving mode, the predetermined receive electronics portion operates less frequently when it is collecting and or processing the data from the middle or far range when compared with the near range. Lastly, the imaging system saves power by modifying the operation as the predetermined receive electronics portion collects or process the data depending upon the active aperture and/or the update depth. In the third power saving mode, the predetermined receive electronics portion operates at least less frequently when it is collecting and or processing the data from the outside the active aperture and or at a far update depth. In other words, the third power saving mode is a hybrid or combination of the first and second power saving modes.

Now referring to FIG. 7, a diagram illustrates a varying decimation rate of the decimator unit 122 at different update depths in the second embodiment of the ultrasound imaging system according to the current invention. In one implementation of the second embodiment, the ADC Clock Rate signal determines an ADC sampling rate at the analog-to-digital conversion (ADC) unit 120', and the ADC Clock Rate signal as shown at the top right of FIG. 7 is used as a constant rate across the update depths. FIG. 7 also shows the varying Decimation Rates at different update depths on the right-hand side below the ADC Clock Rate.

The left-hand side of FIG. 7 illustrates the update depths with respect to the probe 40. As already described above with respect to FIG. 3, the near field is the shallowest depth range in a subject with respect to the probe 40 from which the ultrasound is received, and its depth ranges between a depth 0 and a predetermined depth 1. The middle field is a depth range between the near field and the far field in the subject, and its depth ranges between the predetermined depth 1 and a predetermined depth 2. The far field is the deepest depth range in the subject with respect to the probe, and its depth ranges between the depth 2 and a predetermined depth 3. These fields are generally not overlapping.

The decimator unit 122 is connected to the ADC 120' for receiving the digital outputs from the ADC 120'. While the ADC 120' performs an analog-to-digital signal conversion on the processed signal based upon the constant ADC Clock Rate across the update depths, the decimator unit 122 processes the number of converted sample outputs from the ADC 120' depending upon the Decimation Rate signal which varies according to the update depth range. That is, the decimator unit 122 reduces a number of the converted sample outputs from the ADC 120' as the update depth range increases in order to have substantially the same effect as changing sampling rates.

Still referring to FIG. 7, in the near, middle and far ranges as indicated along a vertical line VL, the decimator unit 122 selects all of converted sample outputs from the ADC 120' and decimates at a substantially Decimation Rate M=1 in the near field. That is, in the near field, the decimator unit 122 discards none of the converted sample outputs from the ADC 120'. The sane decimator unit 122 selects at a second Decimation Rate N in the middle field and decimates the rest of the converted sample outputs from the ADC 120'. Lastly, the decimator unit 122 selects at a third Decimation Rate P, which is less than the second Decimation Rate N and decimates the rest of the converted sample outputs from the ADC 120'.

Now referring to FIG. 8, a diagram illustrates a varying Sample Interpolation Rate of the sample interpolation unit 140' at different update depths in the second embodiment of the ultrasound imaging system according to the current invention. The left-hand side of FIG. 8 illustrates the update depths with respect to the probe 40. As already described above with respect to FIG. 3, the near field is the shallowest depth range in a subject with respect to the probe 40 from which the ultrasound is received, and its depth ranges between a depth 0 and a predetermined depth 1. The middle field is a depth range between the near field and the far field in the subject, and its depth ranges between the predetermined depth 1 and a predetermined depth 2. The far field is the deepest depth range in the subject with respect to the probe, and its depth ranges between the depth 2 and a predetermined depth 3. These fields are generally not overlapping.

The sample interpolation unit 140' is connected to the beamformer sample selection block 130' for receiving the selected digital outputs from the beamformer sample selection block 130'. The sample interpolation unit 140' interpolates the data based upon the selected sample outputs from the beamformer sample selection block 130' depending upon the Sample Interp Select signal which varies according to the update depth range.

Still referring to FIG. 8, in the near, middle and far ranges as indicated along a vertical line VL, the sample interpolation unit 140' utilizes selected sample outputs including sample outputs A1 and A5 from the beamformer sample selection block 130' and interpolates the data A2, A3 and A4 in the near field. The sample interpolation block uses ALL input samples. The same sample interpolation unit 140' utilizes selected sample outputs B1 and B3 from the beamformer sample selection block 130' and interpolates the data B2 in the middle field. Lastly, the sample interpolation unit 140' does not interpolate data in the far field (or interpolates at an even lower rate than the middle rate). The above example illustrates power saving in a beamformer by reducing an amount of the data in the beamformer as well as in a beam summation interface. As the update depth increases, the less amount of data is necessary since the sidelobe effects of utilizing lower interpolation become less significant.

Now referring to FIG. 9, diagrams illustrate another power saving scheme based upon a combination of the active aperture and the update depth in a third embodiment of the ultrasound imaging system according to the current invention. FIG. 9A is a diagram illustrating a varying active aperture on a 2D array 50 to be associated with an analog-to-digital converter (ADC) according to the current invention. The 2D array 50 consists of transducer elements, and the elements are grouped into three array element groups A, B and C. The array element group A is the smallest as indicated in dark color while the array element group C is the largest as indicated in light color. The array element group B is between the two groups in size as indicated by slanted lines. The active aperture is a concept that defines a certain transducer element boundary at a particular depth in selecting channel signals in the power saving scheme in the ultrasound imaging system according to the current invention. In the illustrated active aperture, the aperture size grows as the update depth increases as will be described below.

FIG. 9B is a timing chart depicting a varying onset of a clock signal to an analog-to-digital converter (ADC) in relation to the update depth according to the current invention. In order to save power, the ADC delays the sampling of the channel signals until the corresponding channel are within a predetermined active aperture at a certain update depth. In the exemplary implementation, three 2D array element groups A, B and C correspond to the three distinct active apertures. At a predetermined time t=0, the 2D array starts receiving signals from an update depth a. In order to ascertain a proper onset of the ADC clock signals Group A at the time t=0, an optional clock start up time may be subtracted from the time t=0 to allow the ADC clock signals Group A to reach equilibrium as indicated by a gray block. When the ADC receives the ADC clock signals Group A, the ADC samples the channel signals from the array element group A.

Still referring to FIG. 9B, after a first predetermined delay period at a predetermined time t=T1, the 2D array starts receiving signals from an update depth b. In order to ascertain a proper onset of the ADC clock signals Group B at the time t=T1, an optional clock start up time is subtracted from the time t=T1 to allow the ADC clock signals Group B to reach equilibrium as indicated by a gray block. When the ADC receives the ADC clock signals Group B, the ADC samples the channel signals from the array element group B due to the predetermined delay.

Lastly, after a second predetermined delay period at a predetermined time t=T2, the 2D array starts receiving signals from an update depth c. In order to ascertain a proper onset of the ADC clock signals Group C at the time t=T2, an optional clock start up time is subtracted from the time t=T2 to allow the ADC clock signals Group C to reach equilibrium as indicated by a gray block. When the ADC receives the ADC clock signals Group C, the ADC samples the channel signals from the array element group C due to the predetermined delay. Consequently, since the ADC performs the analog-to-digital conversion only on the channel signals that are within the active aperture, an embodiment saves power in the ultrasound imaging system according to the current invention.

Figure 10A:
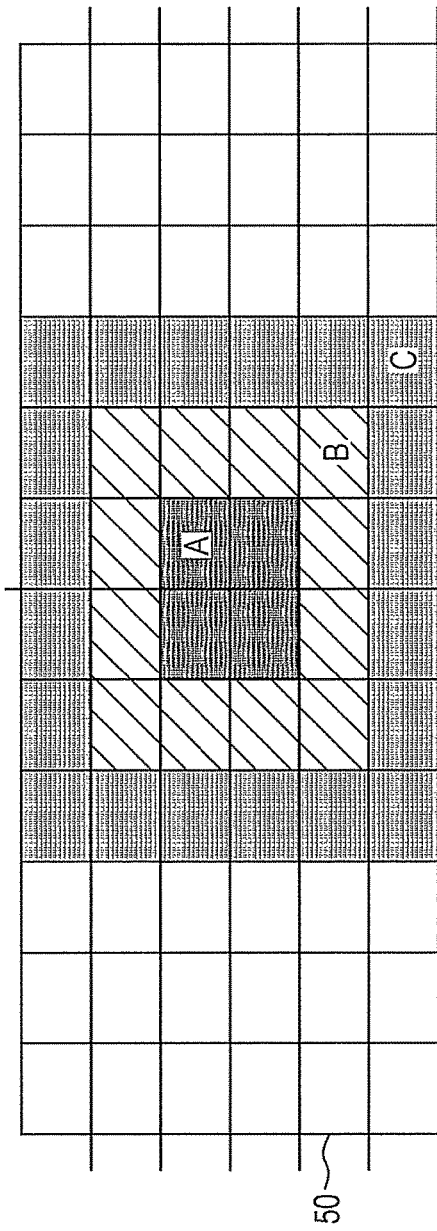
FIG. 10 includes diagrams illustrating another power saving scheme based upon a combination of the active aperture and the update depth in a fourth embodiment of the ultrasound imaging system according to the current invention.

Now referring to FIG. 10, diagrams illustrate another power saving scheme based upon a combination of the active aperture and the update depth in a fourth embodiment of the ultrasound imaging system according to the current invention. FIG. 10A is a diagram illustrating a varying active aperture on a 2D array 50 to be associated with a beamformer sample selection unit according to the current invention. The 2D array 50 consists of transducer elements, and the elements are grouped into three array element groups A, B and C. The array element group A is the smallest as indicated in dark color while the array element group C is the largest as indicated in light color. The array element group B is between the two groups in size as indicated by slanted lines. The active aperture is a concept that defines a certain transducer element boundary at a particular depth in selecting channel signals in a power saving scheme in the ultrasound imaging system according to the current invention. In the illustrated active aperture, the aperture size grows as the update depth increases as will be described below.

Figure 10B:
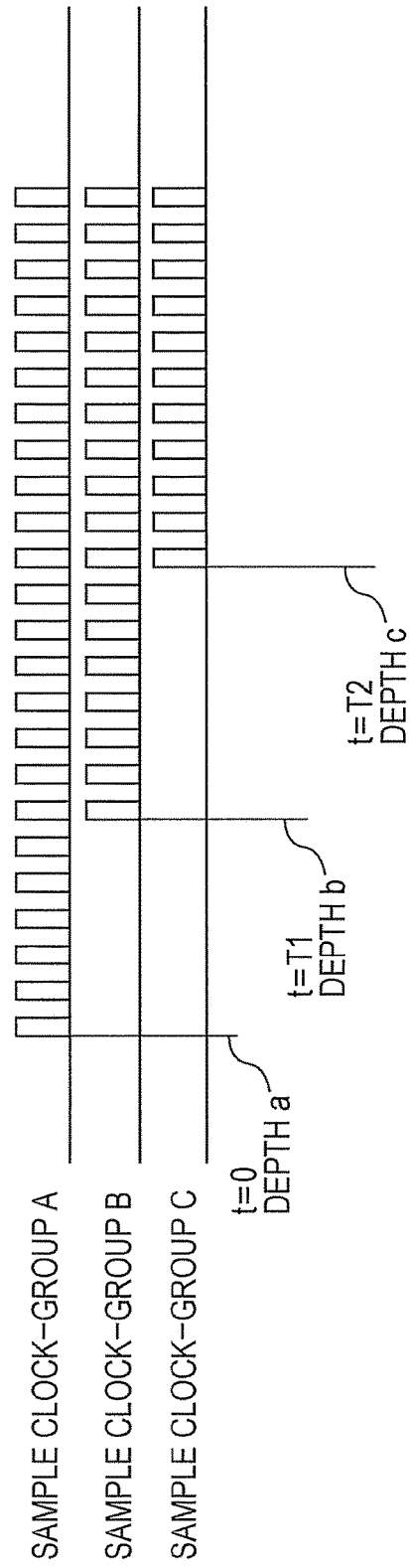

FIG. 10B is a timing chart depicting a varying onset of a sample clock signal to a beamformer sample selection unit in relation to the update depth according to the current invention. In order to save power, the beamformer sample selection unit starts receiving digital beamformer data clocking or the sample clock signal when the corresponding channels are within a predetermined active aperture at a certain update depth. In the exemplary implementation, three 2D array element groups A, B and C correspond to the three distinct active apertures. At a predetermined time t=0, the 2D array starts receiving signals from an update depth a. When the beamformer sample selection unit receives the sample clock signals Group A, the beamformer sample selection unit selects the converted digital data originated from the array element group A.

Still referring to FIG. 10B, after a first predetermined delay period at a predetermined time t=T1, the 2D array starts receiving signals from an update depth b. When the beamformer sample selection unit receives the sample clock signals Group B, the beamformer sample selection unit selects the converted digital data originated from the array element group B due to the predetermined delay.

Lastly, after a second predetermined delay period at a predetermined time t=T2, the 2D array starts receiving signals from an update depth c. When the beamformer sample selection unit receives the sample clock signals Group C, the beamformer sample selection unit selects the converted digital data originated from the array element group C due to the predetermined delay. Consequently, since the beamformer sample selection unit selects the converted digital data that are within the active aperture, an embodiment saves power in the ultrasound imaging system according to the current invention.

Figure 11A:
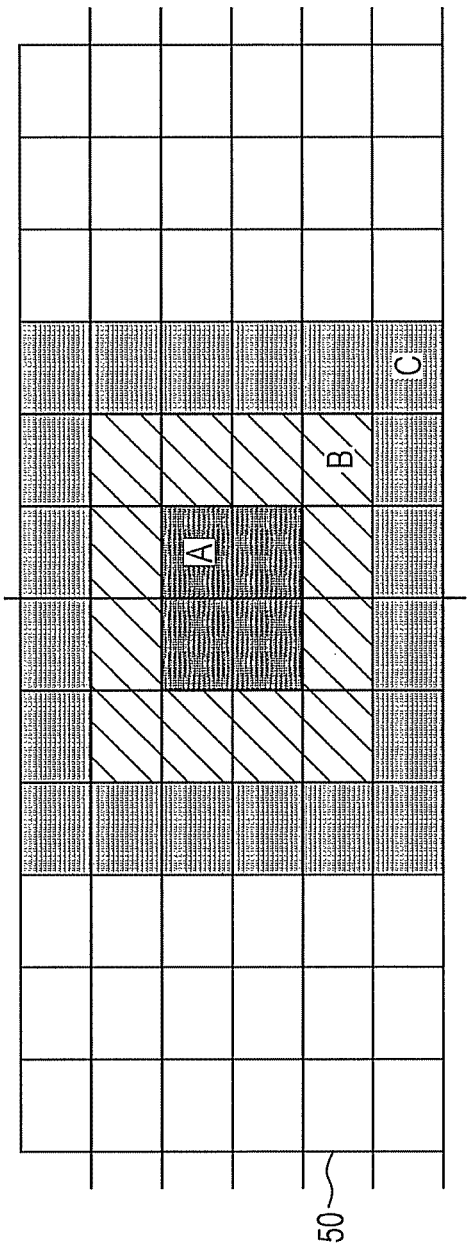
FIG. 11 includes diagrams illustrating another power saving scheme based upon a combination of the active aperture and the update depth in a fifth embodiment of the ultrasound imaging system according to the current invention.

Now referring to FIG. 11, diagrams illustrate another power saving scheme based upon a combination of the active aperture and the update depth in a fifth embodiment of the ultrasound imaging system according to the current invention. FIG. 11A is a diagram illustrating a varying active aperture on a 2D array 50 to be associated with a beamformer sample selection unit and or an analog-to-digital converter (ADC) according to the current invention. The 2D array 50 consists of transducer elements, and the elements are grouped into three array element groups A, B and C. The array element group A is the smallest as indicated in dark color while the array element group C is the largest as indicated in light color. The array element group B is between the two groups in size as indicated by slanted lines. The active aperture is a concept that defines a certain transducer element boundary at a particular depth in selecting channel signals in a power saving scheme in the ultrasound imaging system according to the current invention. In the illustrated active aperture, the aperture size grows as the update depth increases as will be described below.

Figure 11B:
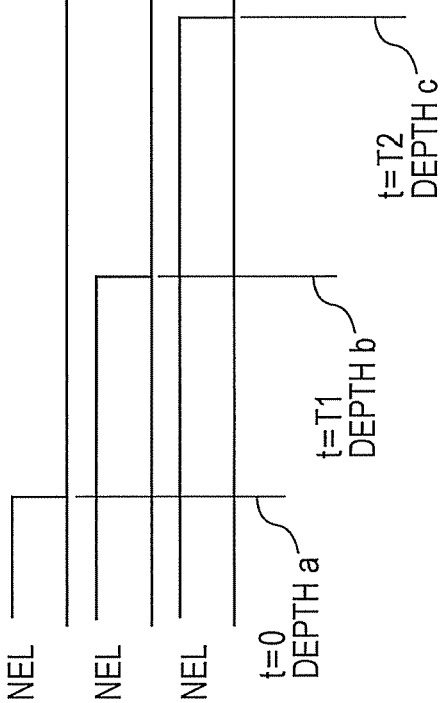

FIG. 11B is a timing chart depicting a varying onset of an ADC channel enable signal and a beamformer (BF) sample channel enable signal respectively to an ADC and a beamformer sample selection unit in relation to the update depth according to the current invention. In order to save power, the ADC and the beamformer output samples are held in a constant state while the corresponding channels are outside of a predetermined active aperture at a certain update depth. In the exemplary implementation, three 2D array element groups A, B and C correspond to the three distinct active apertures. At a predetermined time t=0, the 2D array starts receiving signals from an update depth a. The ADC channel enable signal Group A and the beamformer (BF) sample channel enable signal Group A respectively enables the ADC and the beamformer output samples at the time t=0. Thus, before the ADC and the beamformer output samples are enabled at the time t=0, they hold their output data constant.

Still referring to FIG. 11B, after a first predetermined delay period at a predetermined time t=T1, the 2D array starts receiving signals from an update depth b. The ADC channel enable signal Group B and the beamformer (BF) sample channel enable signal Group B respectively enables the ADC and the beamformer output samples at the time t=T1. Thus, before the ADC and the beamformer output samples are enabled at the time t=T1, they receive no channel signal or channel sample data.

Lastly, after a second predetermined delay period at a predetermined time t=T2, the 2D array starts receiving signals from an update depth c. The ADC channel enable signal Group C and the beamformer (BF) sample channel enable signal Group C respectively enables the ADC and the beamformer output samples at the time t=T2. Thus, before the ADC and the beamformer output samples are enabled at the time t=T2, they receive no channel signal or channel sample data.

Now referring to FIG. 12, a diagram illustrates in a sixth embodiment for processing the ultrasound data while saving power in an imaging system according to the current invention. In the sixth embodiment, the exemplary system includes a first analogue-to-digital converter (ADC1) 120a, a second analogue-to-digital converter (ADC2) 120b, a third analogue-to-digital converter (ADC3) 120c, a fourth analogue-to-digital converter (ADC4) 120d, a decimator block 122a, a beamformer sample selection block 130a, a sample interpolation block 140a, a beamformer block 150a, a first clock buffer 170a, a second clock buffer 170b, a clock generator 172 and a beamformation control processor 180. The above functional units or devices are optionally implemented by corresponding hardware parts and software modules in one embodiment. The above functional units are also optionally implemented by hardware units and software modules that do not necessarily correspond to the above enumerated units in another embodiment. Furthermore, all or some of these functional units are optionally implemented on the probe according to the current invention.

For the purpose of the current patent application, a power saving unit optionally includes a combination of the first analogue-to-digital converter (ADC1) 120a, the second analogue-to-digital converter (ADC2) 120b, the third analogue-to-digital converter (ADC3) 120c, the fourth analogue-to-digital converter (ADC4) 120d, the decimator block 122a, the beamformer sample selection block 130a, the sample interpolation block 140a, the beamformer block 150a, the first clock buffer 170a, the second clock buffer 170b, the clock generator 172 and the beamformation control processor 180. Although the drawings show four ADC units, the same architecture is applicable to any number of ADC units in other embodiments according to the current invention.

Still referring to FIG. 12, the beamformation control processor 180 is connected to the first ADC1 120a, the second ADC2 120b, a third ADC3 120c, a fourth ADC4 120d, the decimator block 122a, the beamformer sample selection block 130a, the sample interpolation block 140a, the beamformer block 150a, the first clock buffer 170a and the second clock buffer 170b. Via the above connections, the beamformation control processor 180 independently provides a combination of a control signal and a channel enable signal to each of the first ADC1 120a, the second ADC2 120b, the third ADC3 120c, the fourth ADC4 120d, the decimator block 122a, the beamformer sample selection block 130a, the sample interpolation block 140a, the beamformer block 150a, the first clock buffer 170a and the second clock buffer 170b. In general, the control signal optionally includes a clock rate signal and other parameters while the channel enable signal enables a corresponding device. That is, if a device or unit is not enabled by the channel enable signal, the device or unit does not perform a predetermined function for the channel.

The analog-to-digital signal converters (ADC1 through ADC4) 120a, 120b, 120c and 120d selectively perform analog-to-digital signal conversion on the channel signals. A resolution level of the analog-to-digital conversion is related to a ratio between a reduced number of output channels and an original number of input channels in the connecting or switching operation. In addition, as will be further discussed for the power saving purposes, the ADC1 through ADC4 120a, 120b, 120c and 120d selectively perform the ADC conversion based upon a predetermined set of conditions that are specified in the clock buffer 170a or 170b by a combination of the channel enable signal from the beamformation control processor 180 and a clock signal from the clock generator 172. In one exemplary implementation as illustrated in FIG. 12A, the above described power saving analog-to-digital signal converters (ADC1 and ADC2) 120a, 120b are both connected as a group to the clock buffer 170a, which in turn receives a combination of a control signal from the clock generator 172 and a channel enable signal from the beamformation control processor 180. In this implementation, the analog-to-digital signal converters (ADC1 and ADC2) 120a, 120b are operated in the same manner.

In another exemplary implementation as illustrated in FIG. 12B, the above described power saving analog-to-digital signal converters (ADC3 and ADC4) 120c, 120d are independently connected to the clock buffer 170b, which in turn receives a combination of a control signal from the clock generator 172 and a channel enable signal from the beamformation control processor 180. In this implementation, the analog-to-digital signal converters (ADC1 and ADC2) 120a, 120b are independently operated so that the analog-to-digital signal converters are grouped in a desired pattern.

In either implementation in FIG. 12A or 12B, the ADC1 through ADC4 120a, 120b, 120c and 120d are controlled to save power in a predetermined manner. For example, unless the ADC3 unit 120c is selectively enabled by the corresponding channel enable signal when a certain channel is inside a predetermined active aperture, the ADC3 unit 120c fails to convert the analog input data. In one implementation, a ADC clock Rate signal from the clock generator 172 determines an ADC sampling rate at the ADC3 120c, and the ADC clock rate signal has a constant rate across the update depths.

In the sixth embodiment of the ultrasound imaging system according to the current invention, the decimator unit 122a is connected to the ADC1 through ADC4 120a, 120b, 120c and 120d for receiving the digital outputs. The decimator unit 122a is also connected to the beamformation control processor 180 to receive a combination of a decimator control signal. The decimator unit 122a further processes a number of converted sample outputs from the ADC1 through ADC4 120a, 120b, 120c and 120d depending upon a decimation rate signal which may reflect the update depth. That is, the decimator unit 122a reduces a number of the converted sample outputs from the ADC1 through ADC4 120a, 120b, 120c and 120d as the update depth increases in order to have substantially the same effect as changing sampling rates if the ADC clock rates are constant across the update depths.

By the same token, as the beamformer sample selection block 130a receives the selected converted digital data from the decimator unit 122a, the beamformer sample selection block 130a also selectively accepts the converted data based upon a predetermined set of conditions that are specified by a pair of a sample control signal and a channel enable signal from the beamformation control processor 180. For the power saving purposes, unless the beamformer sample selection block 130a is enabled by the channel enable signal when a certain channel is inside a predetermined active aperture, the beamformer sample selection block 130a receives no converted channel sample data from the decimation unit 122*a* and holds its output state constant. In this way, the beamformer sample selection block 130*a* optionally functions as a power-saving gate for the down stream blocks which include the sample interpolation block 140*a* and the beamformer block 150*a*.

Further down the stream from the beamformer sample selection block 130*a*, the sample interpolation block 140*a* selectively interpolates the selected beamformer sample data based upon a sample interpolate selection control signal. That is, the sample interpolation unit 140*a* interpolates the selected beamformer sample data from the beamformer sample selection unit 130*a* to economize the interpolation process for the power saving purposes. In one implementation, the sample interpolation block 140*a* saves power by reducing an amount of the data in the beamformer as well as in a beam summation interface. As the update depth increases, the sample interpolation block 140*a* creates a smaller amount of data as the update depth increases since the sidelobe effects become less significant with increasing depth.

In addition, the beamformer block 150*a* selectively generates summation data from the interpolated beamformer sample data from the sample interpolation block 140*a* based upon a predetermined set of conditions that are specified by a pair of a beam formation control signal and a channel enable signal. That is, for the power saving purposes, unless the beamformer channel is enabled by the channel enable signal, the beamformer 150*a* generates no summation data from the interpolated sample data from the sample interpolation block 140*a*. In other words, the beamformer 150*a* economizes the summation data generation for the power saving purposes.

The above described embodiment according to the current invention saves power in processing the data to generate images. In general, the embodiment saves power in overall receiver operations for probe electronics. Furthermore, the embodiment will apply the saved power to any combination of 1) increasing power in various stages, 2) reducing overall power requirements, 3) increasing dynamic range and 4) increasing signal-to-noise ratio. The application of the saved power is not limited to the above illustrated applications.

In general, power is saved in relation to a predetermined active aperture and or a predetermined update depth. With respect to a predetermined active aperture, the imaging system saves power by reducing or turning off a predetermined portion of the receive electronics when the predetermined receive electronics portion is not operating within the active aperture range. That is, in a first power saving mode, the predetermined receive electronics portion operates only when it is collecting and or processing the data inside the active aperture range. Furthermore, with respect to a predetermined update depth, the imaging system saves power by reducing the operational frequency as the predetermined receive electronics portion collects or process the data from a deeper area. That is, in a second power saving mode, the predetermined receive electronics portion operates less frequently when it is collecting and or processing the data from the middle or far range than the near range. Lastly, the imaging system saves power by modifying the operation as the predetermined receive electronics portion collects or process the data depending upon the active aperture and or the update depth. That is, in a third power saving mode, the predetermined receive electronics portion operates at least less frequently when it is collecting and or processing the data from the outside the active aperture and or at a deeper update depth. In other words, the third power saving mode is a hybrid or combination of the first and second power saving modes.

Now referring to FIG. 13, a flow chart illustrates an exemplary process involving steps in saving power in an ultrasound imaging system according to the current invention. The method of saving power according to the current invention is not limited to the disclosed steps, and these steps are merely exemplary to illustrate one implementation of the process. Furthermore, the processes are optionally implemented by utilizing a combination of the devices, units and components of the embodiments of the systems according to the current invention.

Still referring to FIG. 13, an exemplary process generally relies upon a set of predetermined depths and initiates a combination of predetermined operations for saving power at each of the predetermined depths. An exemplary process utilizes a pair of a current depth pointer and an action depth pointer for saving power. The current depth is optionally implemented as a list of the predetermined current depths and a current depth pointer that points to one of the predetermined current depths where the process receives the echoes. On the other hand, the action depth is optionally implemented as a list of the predetermined action depths and an action depth pointer that points to one of the predetermined action depths where an update operation should take place. In a step S100, the exemplary process initiates the current depth pointer and the action depth pointer respectively to a predetermined initial depth. In a step S110, the current depth pointer is incremented by a predetermined depth. In a step S120, the current depth pointer is compared to the action depth pointer to determined whether or not they point to the same depth. That is, if the step S120 determines that the current depth matches the action depth, the exemplary process performs a combination of the power saving operations for the particular update depth. Any of these power saving operations is independently performed in the exemplary process as will be further described. On the other hand, if the step S120 determines that the current depth fails to match the action depth, the exemplary process, the preferred process proceeds to an end check step S190. If it is determined in the step S190 that the current depth pointer fails to point to the predetermined last or deepest depth, the preferred process returns to the update current depth pointer step S110. On the other hand, if is determined in the step S190 that the current depth pointer points to the predetermined last or deepest depth, the preferred process ends its process.

Still referring to FIG. 13, once it is determined in the step S120 that the current depth matches the action depth, a series of the update steps subsequently take place in the exemplary process. These update steps include an update action depth step S130, where the action depth pointer is now incremented to a next action depth in the action depth list. At the same time, the update steps also include a channel enable depth list step S140, where the current action depth value is compared to a list of predetermined channel enable depths. If the current action depth value is indeed one of the predetermined channel enable depths, the associated parameters are used in an update enable step S142 to enable the corresponding units or devices. For example, the update enable step S142 enables an analog-to-digital converter and a beamformer sample selection unit according to the parameter from the step S140. After the update enable step S142, the preferred process proceeds to the end check step S190. If it is determined in the step S190 that the current depth pointer fails to point to the predetermined last or deepest depth, the preferred process returns to the update current depth pointer step S110. On the other hand, if is determined in the step S190 that the current depth pointer points to the predetermined last or deepest depth, the preferred process ends its process.

Furthermore, the duration of enabled channels (i.e., channel enable times) are quantized based on the update frequency in one exemplary process according to the current invention. In this regard, channel enable times are refinement on the channel enabled depth at which a particular channel turns on. The depth is predetermined. The update frequency determines how that depth is quantized to a specific depth within one clock cycle of the update time increment. To illustrate the quantization with one clock cycle of the update time increment, assuming that a predetermined update depth is at 1 cm, it takes the ultrasound echo to 12.98701 microseconds ($\mu$ sec) to travel the round trip distance of 2 cm since the speed of sound is 1540 m/sec. Furthermore, if it is assumed that the update frequency is 10 MHz, the quantization is 100 nanosecond. Thus, in this example, during the time that the ultrasound echo travels the distance over 2 cm, a number of clocks is approximately 1,2988,701 (12.98701/0.01) clocks.

By the same token, once it is determined in the step S120 that the current depth matches the action depth, the preferred process also independently performs a decimation depth list step S150, where the current action depth value is compared to a list of predetermined decimation depths. If the current action depth value is indeed one of the predetermined decimation depths, the associated parameters are used in a decimation update step S152 to perform a predetermined decimation operation. For example, in the decimation update step S152 a decimation unit performs to throws away certain samples according to the parameter from the step S150. After the update decimation step S152, the preferred process proceeds to the end check step S190. If it is determined in the step S190 that the current depth pointer fails to point to the predetermined last or deepest depth, the preferred process returns to the update current depth pointer step S110. On the other hand, if is determined in the step S190 that the current depth pointer points to the predetermined last or deepest depth, the preferred process ends its process.

Similarly, once it is determined in the step S120 that the current depth matches the action depth, the preferred process further independently performs a samples depth list step S160, where the current action depth value is compared to a list of predetermined samples depths. If the current action depth value is indeed one of the predetermined samples depths, the associated parameters are used in a update samples step S162 to perform a predetermined sample selection operation. For example, in the update sample step S162 a sample selection unit performs to select certain samples according to the parameter from the step S160. After the update samples step S162, the preferred process proceeds to the end check step S190. If it is determined in the step S190 that the current depth pointer fails to point to the predetermined last or deepest depth, the preferred process returns to the update current depth pointer step S110. On the other hand, if is determined in the step S190 that the current depth pointer points to the predetermined last or deepest depth, the preferred process ends its process.

In addition, once it is determined in the step S120 that the current depth matches the action depth, the preferred process further independently performs an interpolation depth list step S170, where the current action depth value is compared to a list of predetermined interpolation depths. If the current action depth value is indeed one of the predetermined interpolation depths, the associated parameters are used in an update interpolation step S172 to perform a predetermined sample interpolation operation. For example, in the update interpolation step S172, an interpolation unit performs to interpolate certain samples based upon a number of samples according to the parameter from the step S170. After the update interpolation step S172, the preferred process proceeds to the end check step S190. If it is determined in the step S190 that the current depth pointer fails to point to the predetermined last or deepest depth, the preferred process returns to the update current depth pointer step S110. On the other hand, if is determined in the step S190 that the current depth pointer points to the predetermined last or deepest depth, the preferred process ends its process.

Lastly, once it is determined in the step S120 that the current depth matches the action depth, the preferred process further independently performs a beamformation depth list step S180, where the current action depth value is compared to a list of predetermined beamformation depths. If the current action depth value is indeed one of the predetermined beamformation depths, the associated parameters are used in a update beamformation step S182 to perform a predetermined beamformation operation. For example, in the update beamformation step S182, a beamformation unit performs beamformation based upon a number of samples according to the parameter from the step S180. After the update interpolation step S182, the preferred process proceeds to the end check step S190. If it is determined in the step S190 that the current depth pointer fails to point to the predetermined last or deepest depth, the preferred process returns to the update current depth pointer step S110. On the other hand, if is determined in the step S190 that the current depth pointer points to the predetermined last or deepest depth, the preferred process ends its process.

As described above, the steps S140 through S182 are independently performed based upon each of the comparison results in the separate depth lists. Consequently, any combination of the steps S142 through S182 is performed in an exemplary process according to the current invention.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope of the inventions.

What is claimed is:

1. A method of saving power in an ultrasound imaging device, comprising the steps of:
   a) transmitting ultrasound pulses from transmit elements of a transducer array towards a region of interest of a subject;
   b) receiving at receiving elements of the transducer array ultrasound echoes that have been reflected from the region of interest of the subject and converting the ultrasound echoes into channel signals;
   c) saving power in the ultrasound imaging device by selectively performing interpolation for data of the channel signals at predetermined update depths with a decreased number of interpolated data, generated by the interpolation, along a depth direction in the region of interest; and d) beamforming by using the data of the channel signals and the interpolated data at reception focal points arranged along the depth direction, wherein the depth direction corresponds to a direction toward a deeper side of the region of interest.

2. The method of saving power in an ultrasound imaging device according to claim 1 wherein said interpolation is eliminated at one of the predetermined update depths.

* * * * *